(12) United States Patent
Stobie et al.

(10) Patent No.: US 6,702,852 B2
(45) Date of Patent: Mar. 9, 2004

(54) METHOD FOR RETROFITTING A HEART VALVE HOLDER

(75) Inventors: Robert Stobie, Mission Viejo, CA (US); Jerry L. Jackman, Tustin, CA (US); Cuong Ton-That, Irvine, CA (US); C. Roger Ekholm, Rancho Santa Margarita, CA (US); Steve Newborg, Riverside, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 0 days.

(21) Appl. No.: 10/127,913

(22) Filed: Apr. 23, 2002

(65) Prior Publication Data

US 2002/0161431 A1 Oct. 31, 2002

Related U.S. Application Data

(60) Division of application No. 09/746,431, filed on Dec. 21, 2000, now Pat. No. 6,409,758, which is a continuation-in-part of application No. 09/626,570, filed on Jul. 27, 2000, now abandoned.

(51) Int. Cl.$^7$ .................................................. A61F 2/06
(52) U.S. Cl. ..................................... 623/2.11; 606/108
(58) Field of Search ......................... 128/898; 606/108; 623/2.11

(56) References Cited

U.S. PATENT DOCUMENTS

| 3,409,013 A | 11/1968 | Berry |
| 3,628,535 A | 12/1971 | Ostrowsky et al. |
| 4,702,250 A | 10/1987 | Ovil et al. |
| 4,865,600 A | 9/1989 | Carpentier et al. |
| 5,476,510 A | 12/1995 | Eberhardt et al. |
| 5,776,187 A | 7/1998 | Krueger et al. |

FOREIGN PATENT DOCUMENTS

| WO | WO 95/17139 A1 | 6/1995 |
| WO | WO 00/40176 A1 | 7/2000 |

*Primary Examiner*—Corrine McDermott
*Assistant Examiner*—Thomas C Barrett
(74) *Attorney, Agent, or Firm*—John Christopher James; Guy L. Cumberbatch

(57) ABSTRACT

An improved holder, system and method for implanting a tissue-type prosthetic heart mitral valve that constricts the commissure posts of the valve and allows the user to detach the handle of the holder prior to withdrawing the holder itself. The ability to remove the handle allows a surgeon greater access to suturing the prosthetic valve to the mitral annulus. The holder may include two relatively movable plates, one of which attaches to the valve sewing on the inflow end of the valve ring and the other which attaches via sutures to the valve commissures on the outflow end. Separation of the plates places the sutures in tension and constricts the commissures. An adjusting member or adapter is interposed between the handle and holder to enable separation of the two plates and removal of the handle. The adjusting member or adapter may be packaged with the valve and holder combination, or may be sold as a separate unit, possibly with the handle, so that prior art holders can be retrofit.

4 Claims, 14 Drawing Sheets

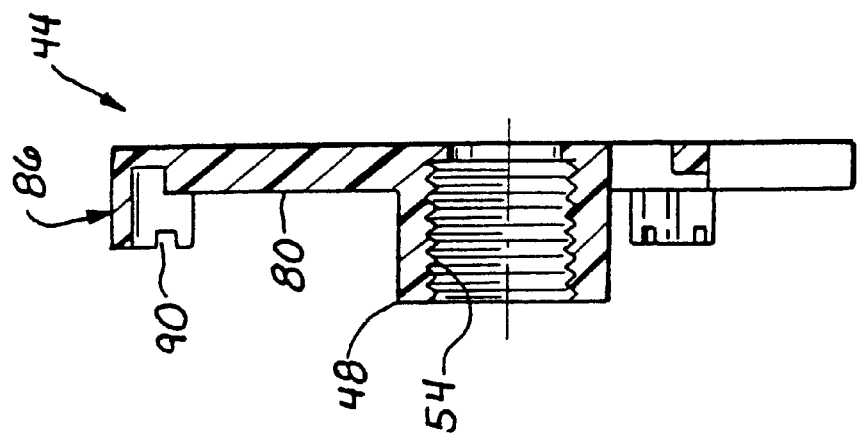
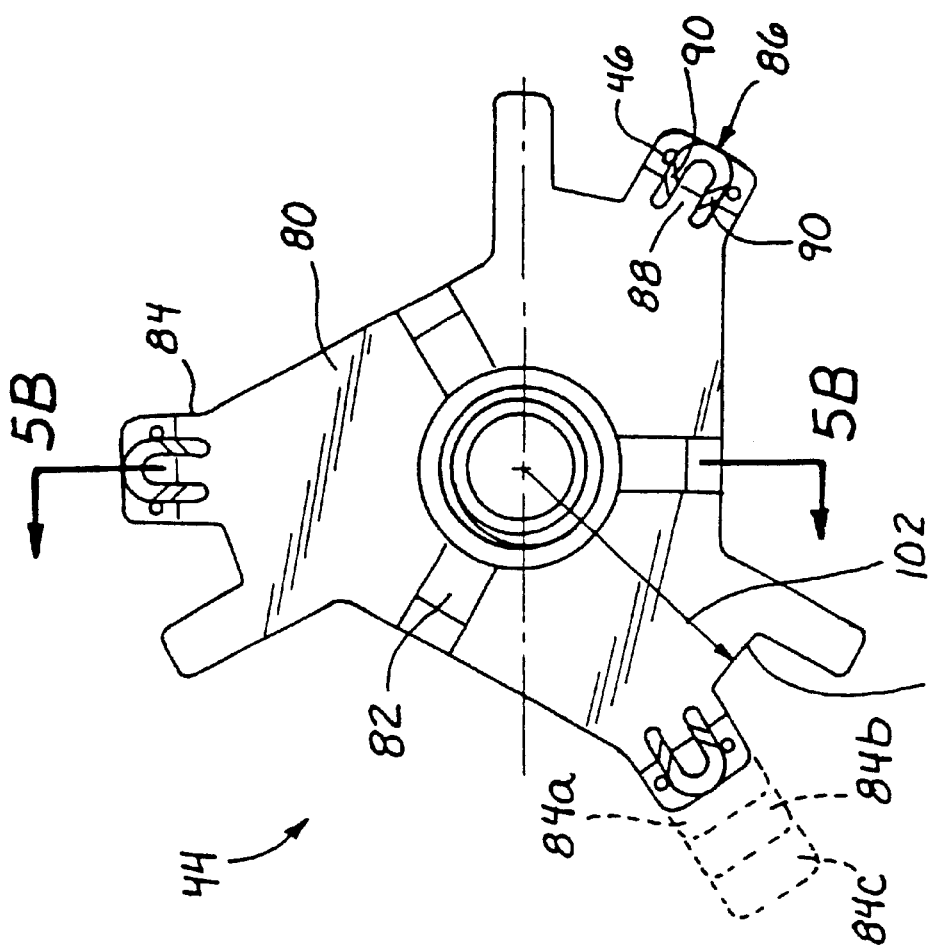

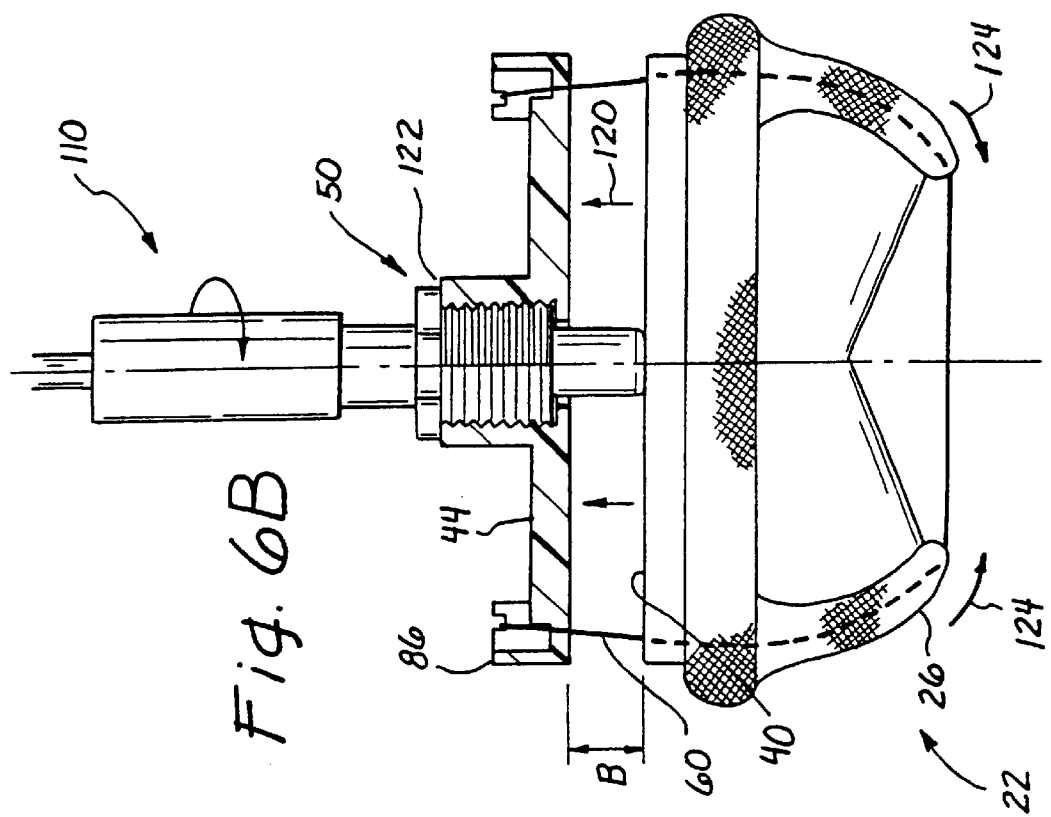
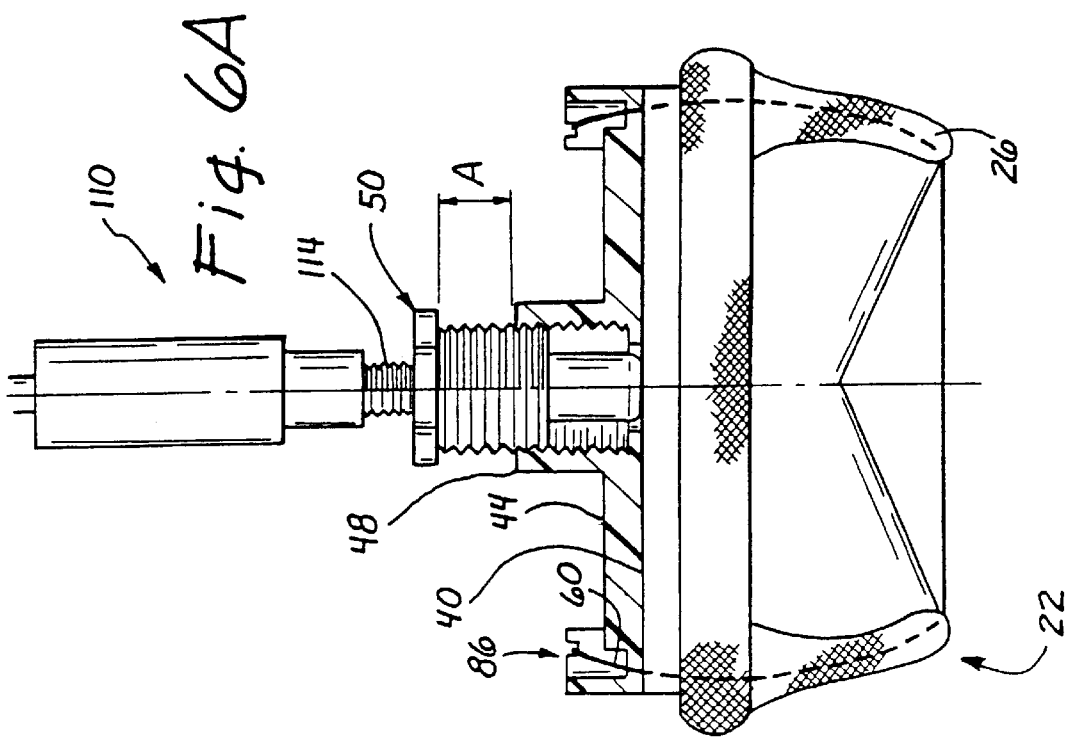

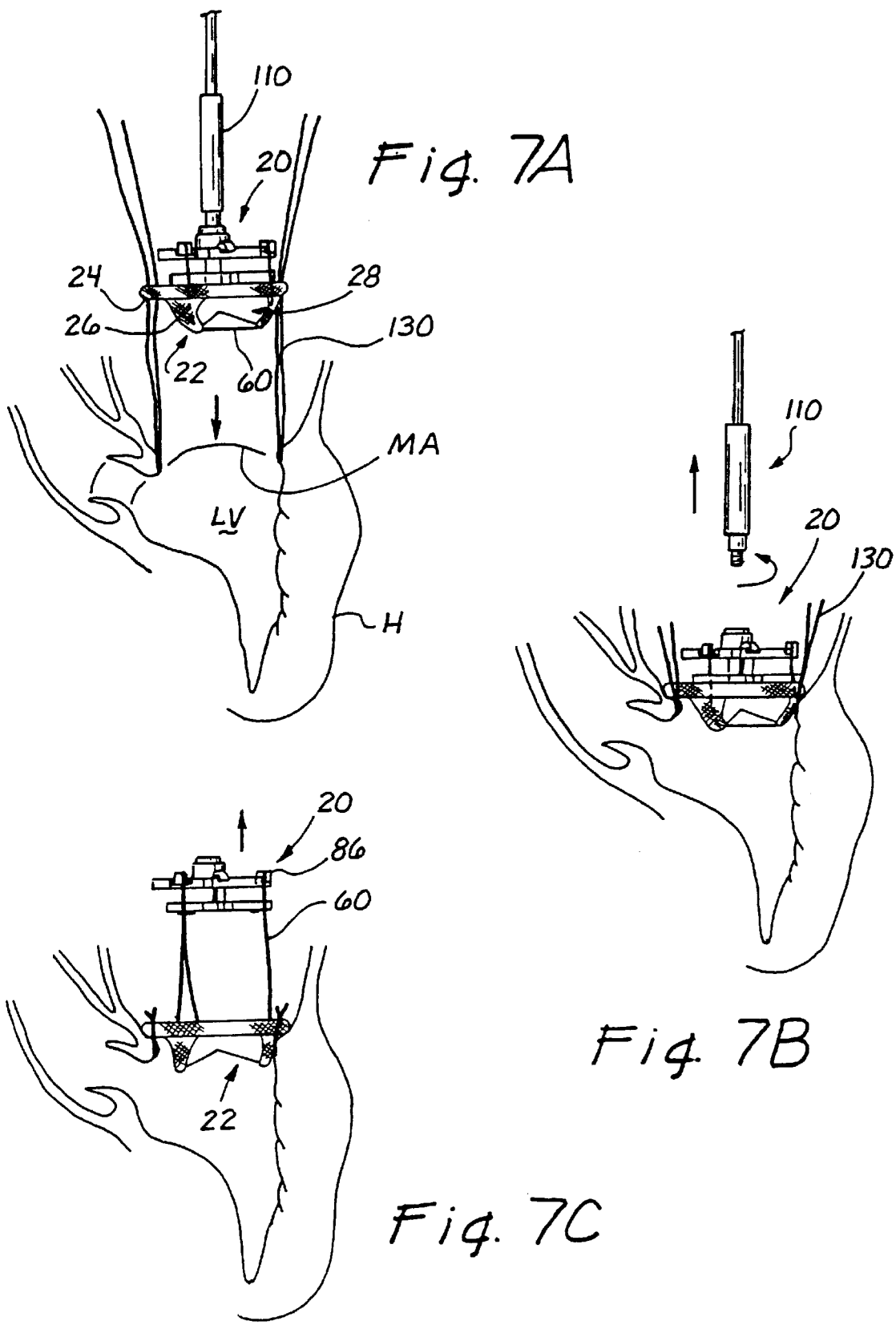

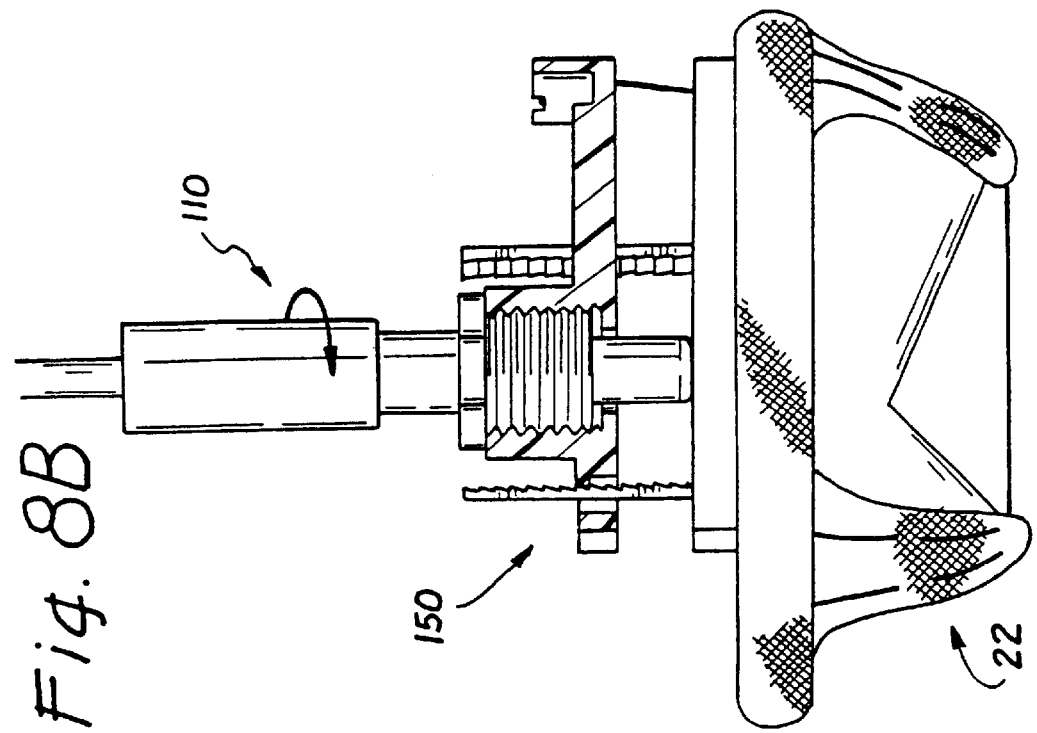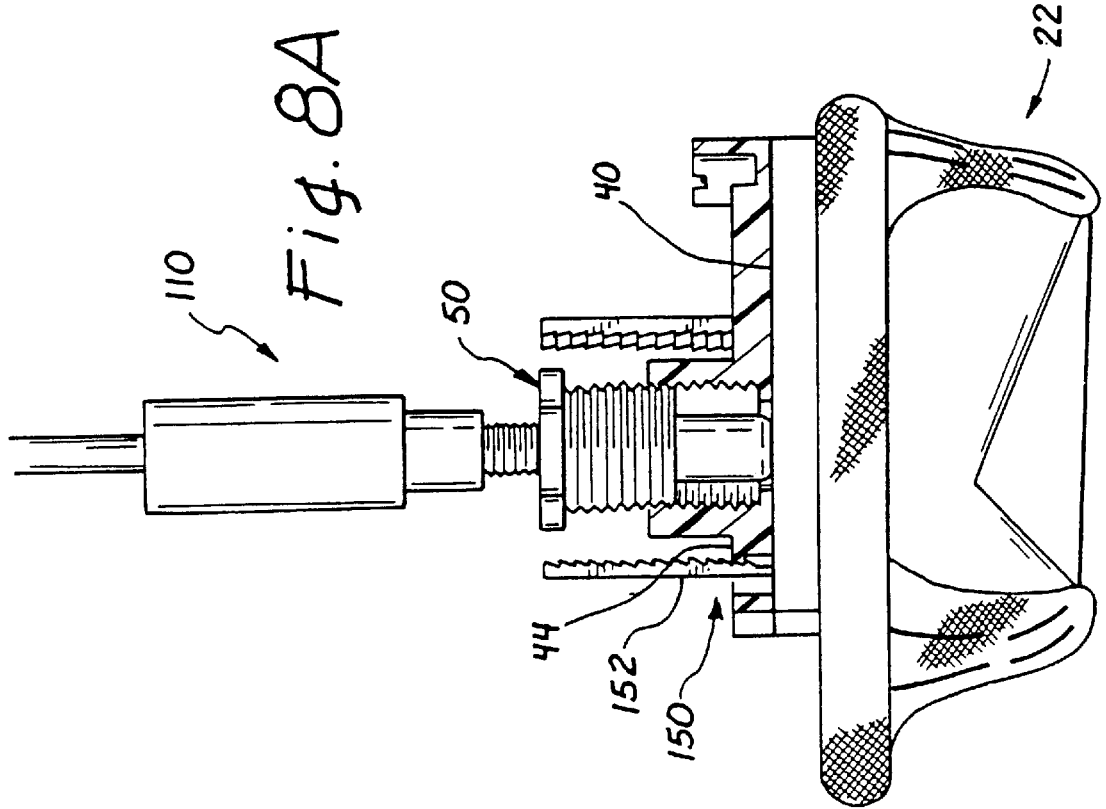

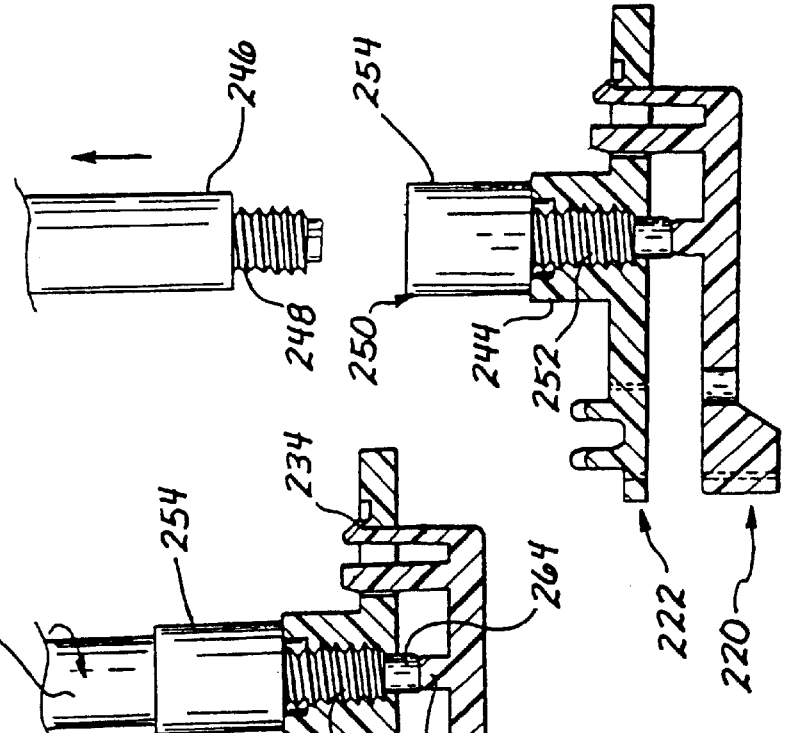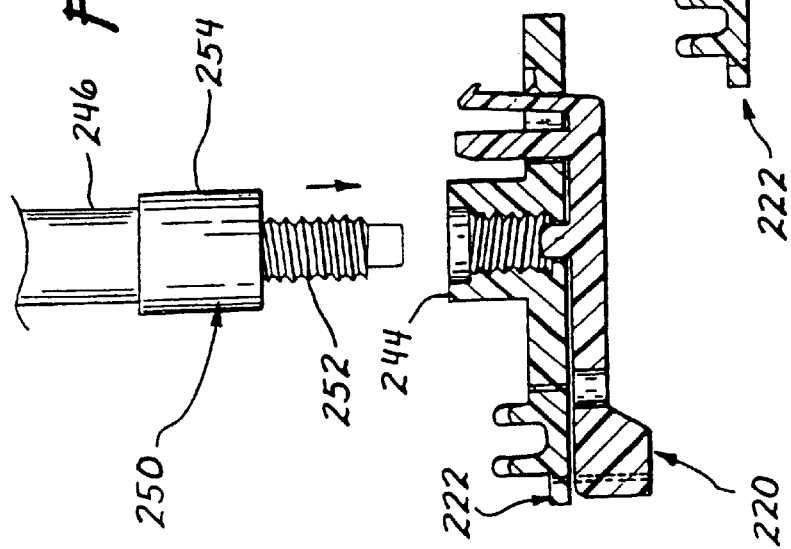

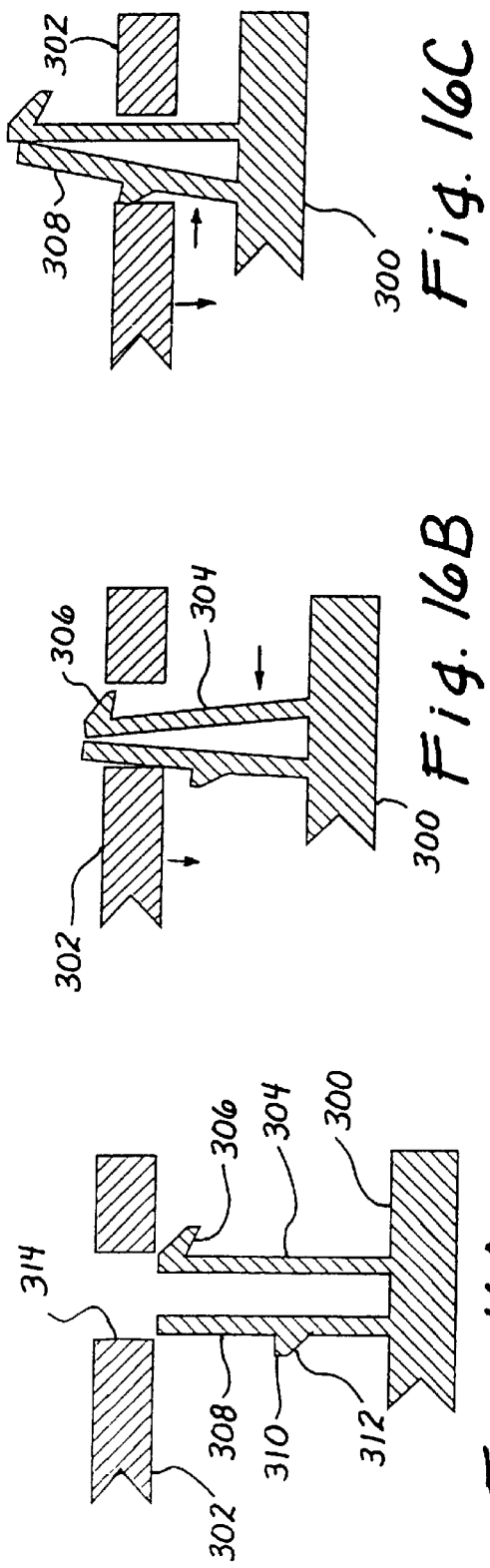
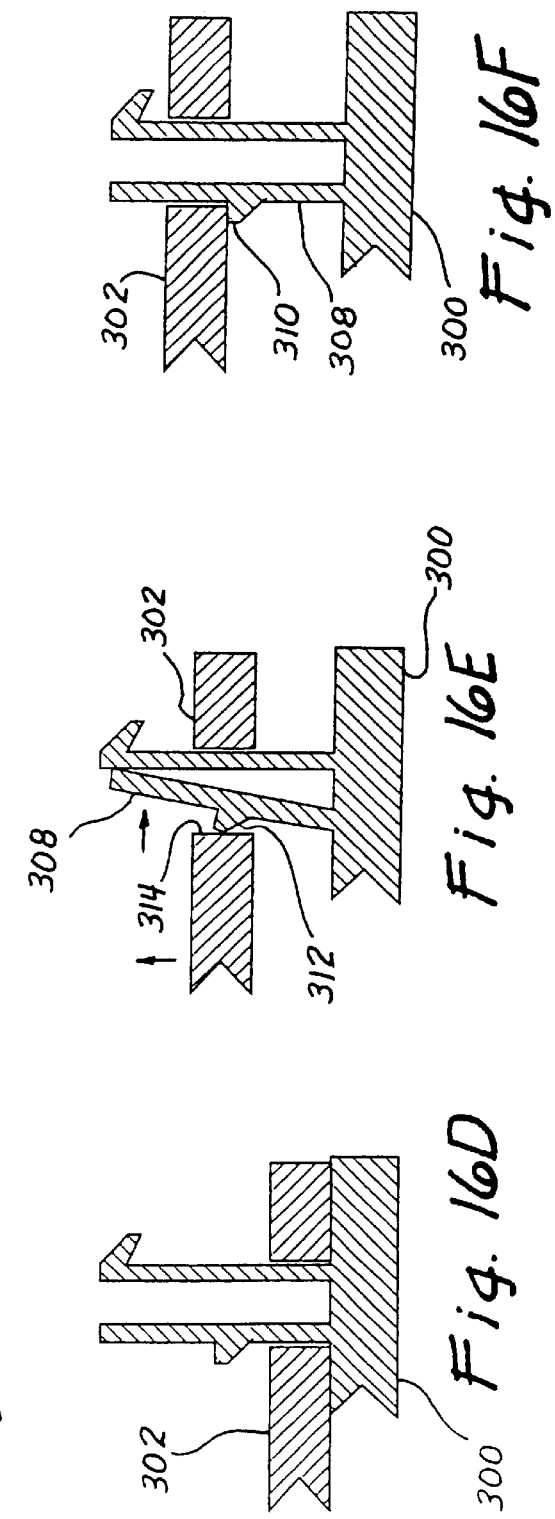

METHOD FOR RETROFITTING A HEART VALVE HOLDER

RELATED APPLICATION

The present application is a divisional of U.S. application Ser. No. 09/746,431, now U.S. Pat. No. 6,409,758 B2 filed Dec. 21, 2000, which is a continuation-in-part of U.S. application Ser. No. 09/626,570, filed Jul. 27, 2000, now abandoned.

FIELD OF THE INVENTION

The present invention relates generally to medical devices, and more particularly to an apparatus for facilitating the implantation of a bioprosthetic replacement heart valve, and associated methodology.

BACKGROUND OF THE INVENTION

In mammalian animals, the heart is a hollow muscular organ having four pumping chambers: the left and right atria and the left and right ventricles, each provided with its own one-way valve. The natural heart valves are identified as the aortic, mitral (or bicuspid), tricuspid and pulmonary valves and have leaflets to control the directional flow of blood through the heart. The valves are each mounted in an annulus that comprises a dense fibrous ring attached either directly or indirectly to the atrial or ventricular muscle fibers. Various surgical techniques may be used to repair a diseased or damaged valve. In a valve replacement operation, the damaged leaflets are excised and the annulus sculpted to receive a replacement valve.

Two primary types of heart valve replacements or prostheses are known. One is a mechanical-type heart valve that uses a ball and cage arrangement or a pivoting mechanical closure to provide unidirectional blood flow. The other is a tissue-type or "bioprosthetic" valve which is constructed with natural-tissue valve leaflets which function much like a natural human heart valve's, imitating the natural action of the flexible heart valve leaflets which form commissures to seal against each other to ensure the one-way blood flow. In tissue valves, a whole xenograft valve (e.g., porcine) or a plurality of xenograft leaflets (e.g., bovine pericardium) provide occluding surfaces that are mounted within a surrounding stent structure. In both types of prosthetic valves, a biocompatible cloth-covered sewing or suture ring is provided on the valve body, for the mechanical type of prosthetic valve, or on the inflow end of the stent for the tissue-type of prosthetic valve.

In placing a tissue type prosthetic valve in the mitral position, the commissure posts are on the blind side of the valve and may become entangled with pre-installed sutures, and may damage the annulus or tissue during delivery. The difficulty of the delivery task is compounded if the surgery is through a minimally-invasive access channel, a technique that is becoming more common. The problem of entanglement is termed "suture looping," and means that the suture that is used to attach or mount the valve to the heart tissue is inadvertently wrapped around the inside of one or more of the commissure post tips. If this occurs, the looped suture may damage one of the tissue leaflets when tightly tied down, or at least may interfere with valve operation and prevent maximum coaptation of the valve leaflets, resulting in a deficiency in the prosthetic mitral valve.

Some attempts have been made to overcome these problems in current holders for prosthetic mitral valves. An example of such a holder is U.S. Pat. No. 4,865,600, Carpentier, et al., incorporated herein by reference. Carpentier provides a holder having a constriction mechanism that constricts the commissure posts inwardly prior to implantation. The Carpentier device provides an elongate handle to both hold the valve/valve holder combination during implantation, as well as to cause the commissure posts to constrict inwardly. The valve is connected to the valve holder by the manufacturer using one or more sutures, and the combination shipped and stored as a unit. During the valve replacement procedure, the surgeon connects the handle to the holder and locks a locking nut to hold the commissure posts at a given constricted position. The surgeon then attaches the sewing ring of the valve to the native valve annulus with an array of sutures that has been pre-embedded in the annulus and extended outside the body. The valve is then advanced along the array of sutures to its desired implantation position and the sutures tied off. When the holder is cut free, the commissure posts are released to expand and the holder may be removed using the handle. The inability to remove the elongate handle while maintaining commissure constriction is a detriment. The handle must be attached to the holder so that the commissure posts remain in a constricted position during attachment of the array of sutures to the sewing ring. This can be awkward for manipulation of the valve/valve holder combination during this time-constrained operation. Further, the relatively wide holder periphery may interfere with the attachment step.

What is needed then is an improved tissue-type prosthetic valve holder attachable to the inflow end of the valve that can constrict the commissure posts with or without a handle being attached, yet provides improved visibility and accessibility to the surgeon during the valve attachment steps.

SUMMARY OF THE INVENTION

The present invention provides a holder for a tissue-type prosthetic heart valve having an inflow end and an outflow end and a flow axis therebetween. The valve includes an annular suture ring at the inflow end attached to a stent having posts circumferentially-spaced about the flow axis that support occluding tissue surfaces of the valve. In this type of valve the posts are cantilevered generally in the outflow direction.

The holder includes a valve abutment portion sized and shaped to abut the suture ring at the inflow end of the valve. The holder further includes a commissure post constriction mechanism adapted to constrict the commissure posts radially inward from a relaxed position to a constricted position when actuated by a handle adapted to operatively connect to the commissure post constriction mechanism. A retaining mechanism is also provided that retains the commissure post constriction mechanism in the constricted position after the handle is removed.

In one embodiment the commissure post constriction mechanism comprises an adjusting portion and an adjusting member adapted to adjust the distance between the adjusting portion and the valve abutment portion and one or more filaments attached to the adjusting portion and sutured through the end of the commissure posts distal the adjusting portion. When the adjusting member is operated to separate the adjusting portion from the valve abutment portion the adjusting portion pulls the filaments, which in turn urge the end of the commissure posts distal the adjusting portion radially inwardly, to the constricted position.

The valve abutment portion may be of a planar shape, with the adjusting portion of a substantially complementary planar shape to the valve abutment portion. It is preferred that the planar shape of the valve abutment portion be comprised of a plurality of tangs radiating from a central body to each cover a portion of the suture ring. In this manner a sufficient amount of the suture ring is left exposed to allow for suturing the suture ring to the native annulus.

Adjustment of the distance between the valve abutment portion and the adjusting portion may be achieved by providing a central threaded aperture in the adjusting portion and an adjusting member that cooperates with this threaded aperture. In this construction the end of the adjusting member proximal the valve abutment portion abuts the valve abutment portion during operation. When the adjusting member is advanced through the central aperture of the adjusting portion it pushes the valve abutment portion and the two portions separate.

A handle may be operatively connected to the adjusting member to turn it by providing a handle that has an externally threaded end portion and an adjusting member having a central longitudinal threaded bore sized to receive the threaded end of the handle. When the handle is introduced into the bore it is rotated in a first direction and will seat in the threaded bore of the adjusting member. Further rotation of the adjusting member separates the adjusting portion from the valve abutment portion, as recited above, and causes the commissure posts to constrict inwardly.

In the prior art the handle would have to remain attached during suturing of the suture ring to the host tissue to keep the commissure posts in the constricted position. The holder with the handle connected were removed by severing the filament(s) and removing the holder, handle and filaments together.

In accordance with the present invention, the adjusting member itself may be adapted to be the retaining mechanism. Preferably, the adjusting member threads create a greater frictional resistance with the threaded aperture of the adjusting portion than that between the threaded end of the handle and the threaded bore of the adjusting member. This frictional resistance between the adjusting member and the central aperture allows the handle to be further rotated in a second, opposite direction, and the handle will detach or unscrew from the adjusting member without moving the adjusting member, leaving the commissure posts in the constricted position. The tug of the filaments themselves on the adjusting portion when the commissure posts will cause the adjusting member/central aperture thread interface to bind and so may be used to achieve the requisite additional frictional resistance required for allowing the handle to be unscrewed.

In alternative embodiments other mechanisms may be used in accordance with the invention to act as the retaining mechanism. For example, a ratchet assembly may be provided to lock the valve attachment and adjusting portions apart, allowing the handle to be removed while leaving the commissure posts in the constricted position. A ratchet assembly may be comprised of a one or more toothed members affixed to the valve abutment portion that each engage a complementary notch, opening or, for example, a pawl affixed to the adjusting portion. As the valve abutment portion and the adjusting portion are separated by the adjusting member the successive teeth of the toothed member engage the notch, opening or pawl affixed to the adjusting portion, locking the two portions apart.

The present invention further provides a method for retrofitting a holder for a tissue-type prosthetic mitral heart valve attachable to a surgical delivery handle. The heart valve is of the type having an inflow end and an outflow end and a flow axis therebetween, and includes an annular suture ring at the inflow end and radially flexible commissure posts circumferentially-spaced around the outflow end that support occluding tissue surfaces of the valve. The holder has a commissure post constriction mechanism releasably attached to the sewing ring at the inflow end of the valve, the mechanism adapted to constrict the valve commissure posts radially inward from a relaxed position to a constricted position when actuated by the delivery handle. The method includes providing a retaining mechanism that retains the commissure post constriction mechanism in the constricted position after the delivery handle is removed. The retaining mechanism may be provided during the holder assembly process so that the retaining mechanism is attached to and shipped as a unit with the prosthetic valve. Alternatively, the retaining mechanism may be provided separately from the holder and valve combination and the method includes coupling the retaining mechanism to the holder at the time of surgical implantation of the valve. The retaining mechanism and delivery handle may be packaged and sold as a unit. The retaining mechanism desirably comprises an adapter that is interposed between and threadingly engaged to the holder and the handle.

Further in accordance with the invention a method for replacing a heart valve is provided, comprising the steps of removing an existing heart valve to leave an annulus of that heart valve, attaching a holder of the invention to a prosthetic tissue-type heart valve and constricting the commissure posts of the prosthetic heart valve with a handle; inserting the valve through the annulus of the heart valve; removing the handle while leaving the commissure posts in the constricted position; suturing the tissue-type heart valve to the heart annulus, and detaching the holder from the prosthetic heart valve.

After suturing the heart valve to the annulus the surgeon severs the filament, causing the posts of the stent to open to the relaxed, operational position. The severing of the filament(s) also releases the holder from the prosthetic heart valve, allowing it to be removed.

A further understanding of the nature and advantages of the present invention are set forth in the following description and claims, particularly when considered in conjunction with the accompanying drawings in which like parts bear like reference numerals.

BRIEF DESCRIPTION OF THE DRAWINGS

FIG. 5A is a plan view of an adjusting portion of the holder of the present invention;

FIG. 5B is a sectional view through the adjusting portion of the holder, take along line 5B—5B of FIG. 5A;

FIGS. 6A and 6B are partial sectional views of the holder of the present invention attached to a heart valve wherein the commissure posts of the valve are, respectively, relaxed and biased inwardly;

FIGS. 7A–7C illustrates several steps in the implantation of a tissue-type valve in the mitral position using the holder of the present invention;

FIGS. 8A and 8B are partial sectional views of an alternative holder of the present invention attached to a heart valve wherein the commissure posts of the valve are, respectively, relaxed and biased inwardly;

FIGS. 13A–13C are sectional views of the holder, handle, and adapter combination of FIG. 12 showing several steps of operation;

FIGS. 16A–16F are several sectional views of a portion of an alternative holder of the present invention showing a further apparatus for maintaining commissure constriction.

DESCRIPTION OF THE PREFERRED EMBODIMENTS

The present invention provides an improved heart valve holder for tissue-type prosthetic heart valves that facilitates implantation and reduces the chance of suture entanglement. The holder of the present invention is particularly useful for prosthetic mitral heart valves having commissure posts on the outflow side supporting flexible leaflets therebetween. The mitral position is such that the outflow side (and commissure posts) projects distally toward the left ventricle during implantation, and thus the holder must be attached to the inflow (i.e., accessible) side of the valve. Delivery of the valve to the mitral position involves sliding the valve down a plurality of sutures that have been pre-installed around the annulus and then passed through the valve sewing ring. The holder of the present invention constricts the commissure posts radially inward and thus helps prevent the posts from becoming entangled in the array of pre-installed sutures. This benefit is thus particular to the situation where the outflow side (and commissure posts) of the heart valve extends distally during delivery, which is the case in the mitral position. Nonetheless, the holder of the present invention may prove useful for the implantation of heart valves in other than the mitral position, and thus the invention may be applicable thereto.

Figure 1:
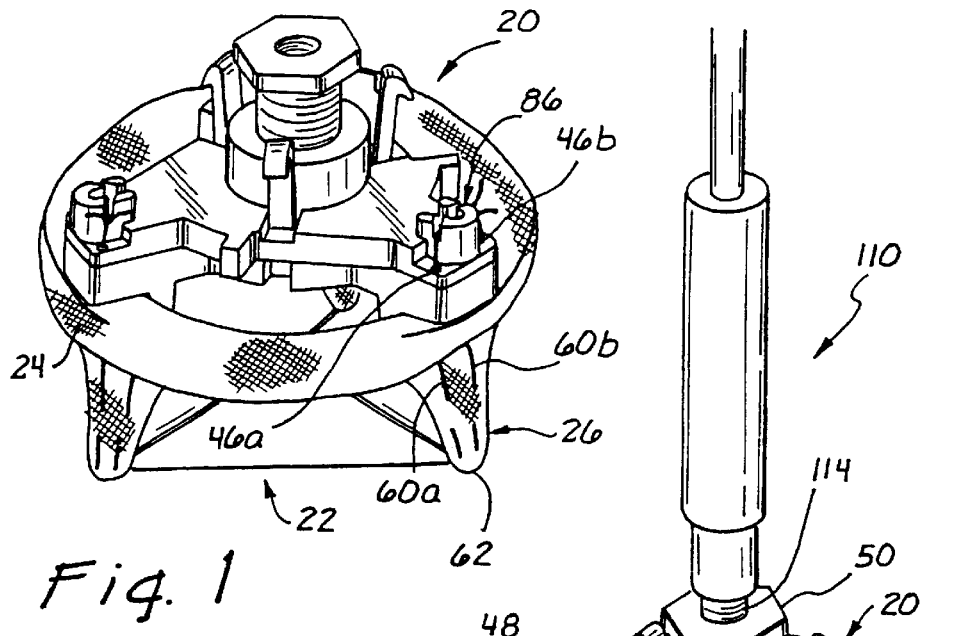
FIG. 1 is a perspective view of a heart valve holder of the present invention assembled to the inflow side of a tissue-type heart valve.
Figure 2:
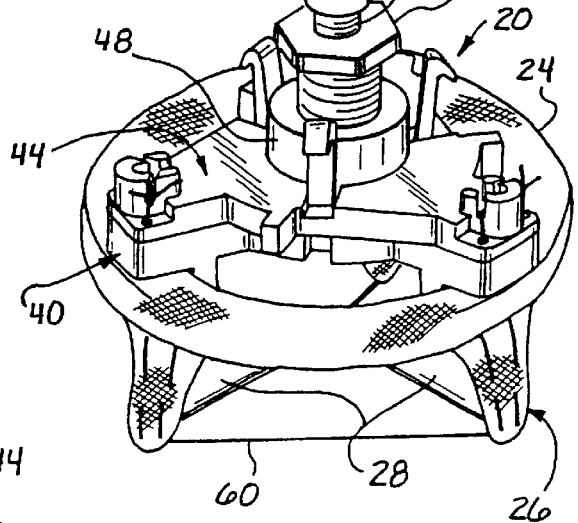
FIG. 2 is a perspective view of the holder/heart valve assembly, showing an actuating and delivery handle attached to the holder.
Figure 3:
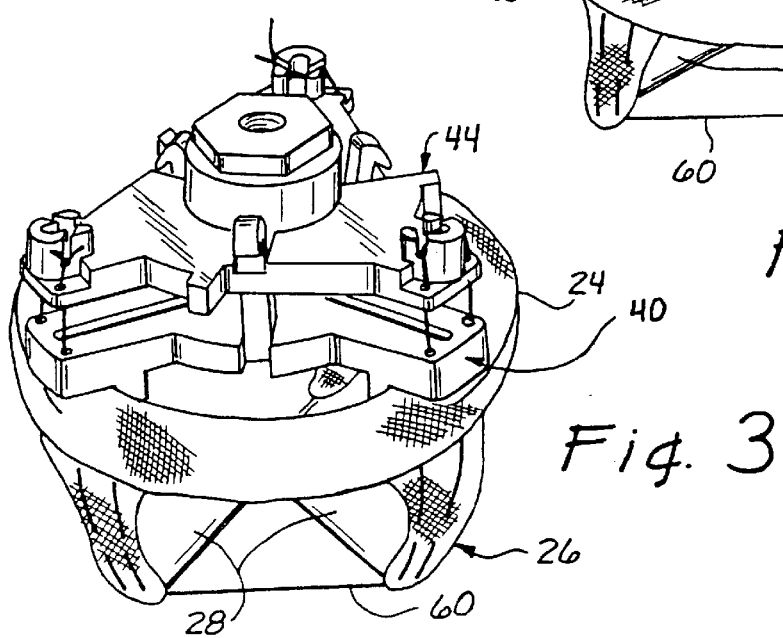
FIG. 3 is a perspective view of the holder/heart valve assembly showing an adjusting portion retracted to cause inward movement of the valve commissure posts.

With reference now to FIGS. 1–3 an exemplary holder 20 of the present invention is shown attached to a tissue-type heart valve 22. The heart valve 22 includes an annular sewing ring 24 on an inflow side, and a plurality of commissure posts 26 projecting generally axially in the outflow direction. The holder 20 attaches to the sewing ring 24 on the inflow side of the valve 22, which also is the proximal (i.e., accessible) side during implantation. That is, commissure posts 26 project distally toward the outflow side of the valve 22.

FIGS. 2 and 3 illustrate a plurality of flexible leaflets 28 that are supported by and extend between the commissure posts 26. The leaflets 28 provide the occluding surfaces of the valve 22, and may be made of individual pieces of bovine pericardium, for example. Alternatively, the leaflets 28 may be part of an entire xenograft, or homograft. In the former instance, natural porcine (pig) valves are particularly useful. Therefore it should be understood that the leaflets 28 may be formed of a variety of materials, none of which is limiting with respect to the present invention. In addition, there are preferably three such leaflets 28 corresponding to three commissure posts 26.

Various constructions for the heart valve 22 are known, which may include metallic or plastic stent elements, a silicone or urethane insert for the sewing ring 24, biocompatible fabric (i.e., polyester) covering around one or more of the elements, etc. In a preferred embodiment, the heart valve 22 includes an internal metallic wireform (not shown) having an undulating shape with a plurality of arcuate cusps connected by upstanding commissures. The wireform commissures provide internal structure for the commissure posts 26 of the valve, and are somewhat flexible so as to be able to flex or cantilever inward. The holder 20 of the present invention facilitates this flexing, though the invention is generally directed toward causing the inward movement of the commissure posts. Of course, other internal constructions of heart valve 22 having movable commissure posts are available, with which the holder 20 of the present invention may function equally as well.

Figure 4:
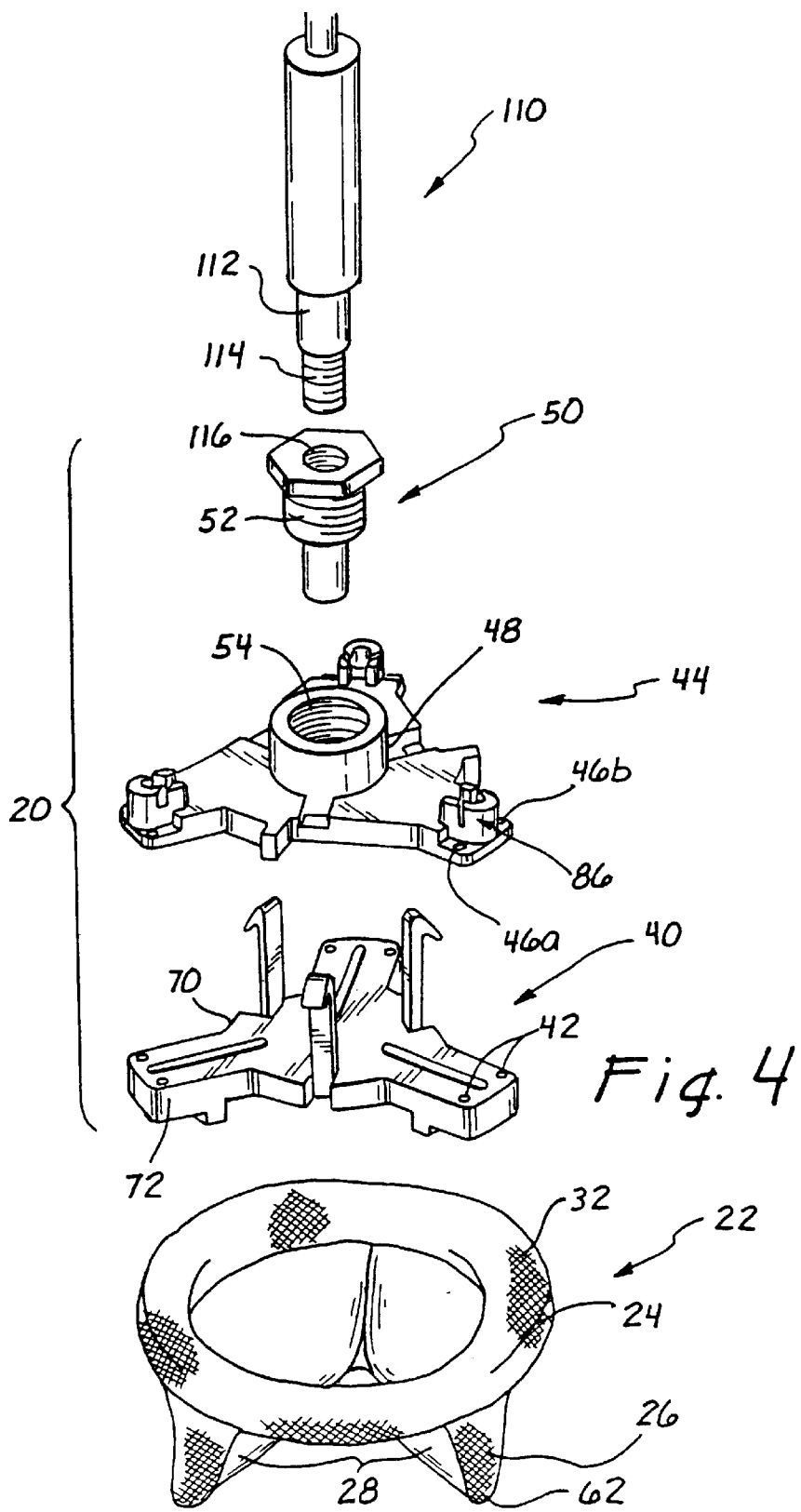
FIG. 4 is a perspective view of the valve holder of the present invention exploded from a tissue-type heart valve.
Figure 9A:
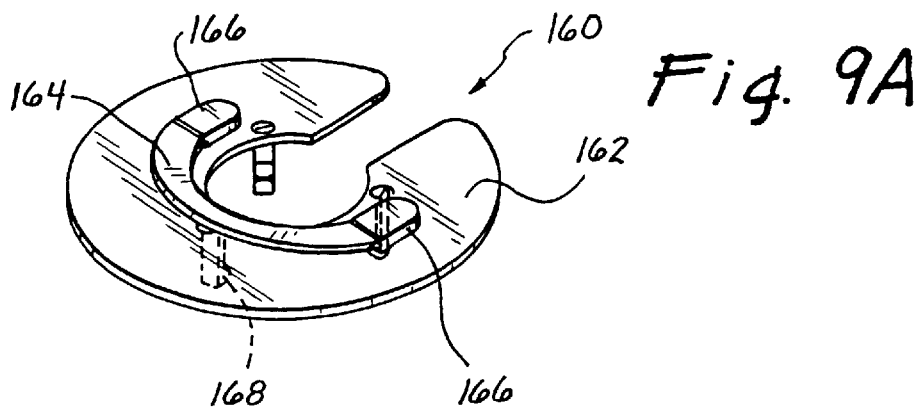
FIG. 9A is a perspective view of an exemplary storage and handling clip that attaches to a holder of the present invention.
Figure 9B:
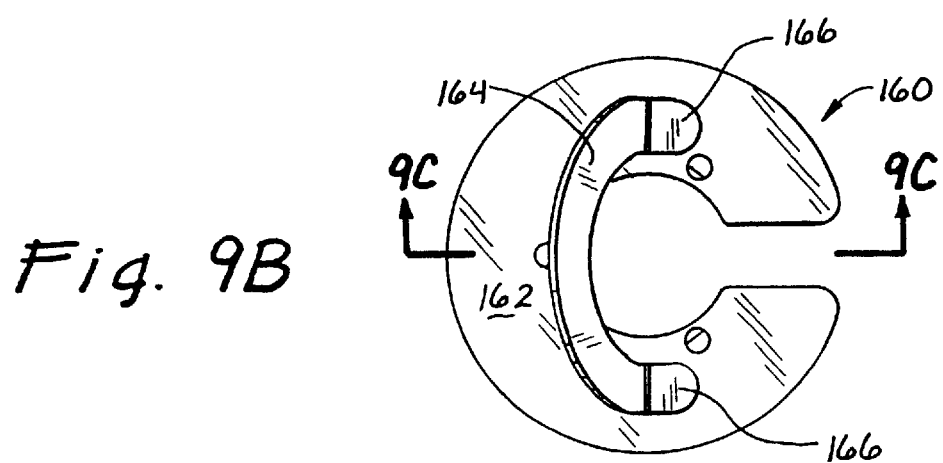
FIGS. 9B–9F are various views of the handling clip of FIG. 9A.
Figure 9C:
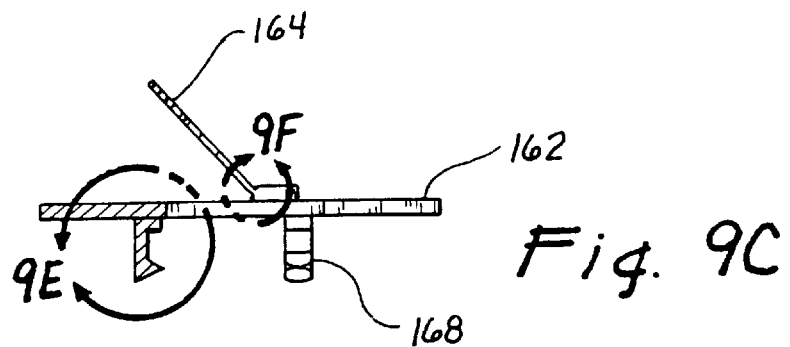
Figure 9D:
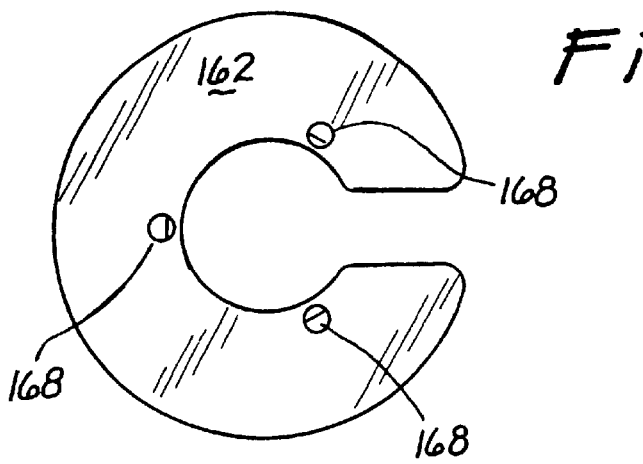
Figure 9E:
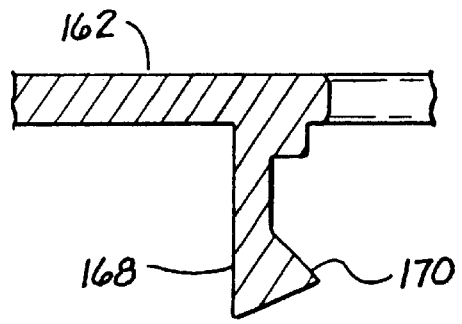
Figure 9F:
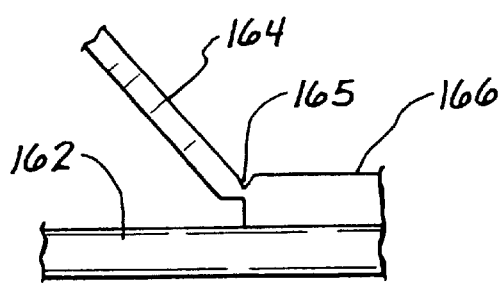

With reference still to FIGS. 1–3, and also FIG. 4, the holder 20 of the present invention includes three relatively movable elements. A plate-like valve abutment portion 40 lies against the inflow side 32 of the sewing ring 24, and includes a plurality of through holes 42 around its periphery. A plate-like commissure adjusting portion 44 generally mirrors the shape of the valve abutment portion 40, and also includes a plurality of peripheral through holes 46. The adjusting portion 44 further includes a centrally located and internally threaded boss 48 that projects in a proximal direction from the otherwise generally planar adjusting portion. Finally, an adjusting member 50 having external threads 52 thereon is sized to mate with the internal threads 54 of the boss 48

A plurality of filaments or sutures 60 are shown in FIGS. 1–3 partly extending between the tips 62 of the commissure posts 26. Because there are three commissure posts 26, there are at least three lengths of sutures 60 extending therebetween in a triangular configuration. Each length of suture 60 spans two of the commissure posts 26, and threads proximally along the post and through the sewing ring 24 to be attached to the holder 20. This is seen best in the perspective view of FIG. 1. Specifically, each suture 60 passes through the holes 42 in the valve abutment portion 40 and attaches to the adjusting portion 44. The specifics of the attachment of each suture 60 will be explained below.

As mentioned, the abutment portion 40, adjusting portion 44, and adjusting member 50 are relatively movable. That is, the adjusting portion 50 is adapted to cause relative axial displacement between the abutment portion 40 and the adjusting portion 44. Because the abutment portion 40 remains against the sewing ring 24, the adjusting portion 44 translates proximally away from the abutment portion, and attached valve 22. This is seen in FIG. 3. Because the sutures 60 attach to the adjusting portion 44, they are also pulled in the proximal direction. Moreover, because each suture 60 threads in a distal direction along and between two of the commissure posts 26, proximal movement of the adjusting portion 44 thus shortens the amount of each suture between the commissure post tips 62. This shortening causes radially inward movement of the tips 62, with the commissure posts 26 eventually flexing inward from their structural point of attachment within the valve 22 adjacent the sewing ring 24.

Now with reference to FIGS. 4 and 5A–5B, structural details of the holder 20 of the present invention will be explained. As mentioned above, the valve abutment portion 40 is generally plate-like, and preferably includes a central, generally triangular body 70 having three outwardly extending tangs 72 at the apices thereof. Two through holes 42 are providing in each of the tangs 72, spaced apart along an imaginary circle centered in the triangular body 70. Three upstanding pins or legs 74 having hooks 76 project from the proximal face of the body 70, preferably inward and between each two tangs 72.

The adjusting portion 44, as best seen in FIG. 5A, also includes a generally triangular plate-like body 80 that is sized similar to the body 70 of the abutment portion 40. In this regard, the adjusting portion 44 includes a plurality of channels 82 on the face opposite the valve abutment portion 40 that received the hooks 76 of the upstanding legs 74 such that the plate-like bodies 70 and 80 can be juxtaposed against one another, though their separation distance is limited. The hooks 76 thus effectively prevent disengagement of the attaching portion 44 and the abutment portion 40 once the two are coupled together. The adjusting portion 44 also includes three outwardly extending tangs 84 at the apices of the triangular body 80. Like the abutment portion 40, two through holes 46 are provided on each of the tangs 84, and are spaced apart along an imaginary circle centered in the body 80. Preferably, each through hole 46 in the adjusting portion 44 aligns with a through hole 42 in the valve abutment portion 40 when the holder 20 is assembled.

Each tang 84 features a suture cutting guide 86 that projects from the proximal face of the body 80. Each cutting guide 86 includes a central cutting recess 88 defined between a pair of suture grooves 90. A cutting recess 88 extends generally radially, while the suture grooves 90 are angled with respect thereto. The depth of the suture grooves 90 is less than the depth of the cutting recess 88, as seen in FIG. 5B, and thus a length of suture 60 can be strung between the grooves 90 so as to be suspended over the cutting recess 88. As seen in FIG. 5A, the suture grooves 90 lead into both of the through holes 46 on either side of the cutting guide 86, such that each suture bridges the cutting recess 88 and may be bent to be secured to or pass through one of the through holes 46. The specific arrangement of the sutures 60 will be more fully described below.

With reference still to FIG. 5A, the adjusting portion 44 further includes means for receiving clips on a removable transport template that secures the holder 20 and heart valve 22 assembly within a storage jar during transportation. Specifically, three clip-receiving notches 100 are equidistantly spaced around the periphery of the body 80. In the illustrated embodiment, the notches 100 are disposed in a counter-clockwise direction adjacent each of the tangs 84 (as seen from the proximal face). Each of the notches 100 is spaced from the center of the body 80 a radial distance 102, as indicated. As seen in the left of FIG. 5A, progressively larger holders will have progressively larger tangs 84a, 84b, 84c so as to enable attachment to larger valve sizes. Advantageously, the notch distance 102 remains constant for all the various sizes of the holder 20 to provide a one-size-fits-all template attachment means. That is, the same size of storage template can be used for a set of different sizes of holders. This arrangement also reduces the radial profile of the holders for larger sized valves, as the dimension of the template notches with respect to the overall perimeter is progressively reduced. This size reduction further helps to prevent snags as the holder and valve are delivered to the implantation site.

With reference again to the perspective views of FIGS. 1–3, the arrangement of the discrete lengths of sutures 60 will now be described. There are desirably three equal lengths of sutures 60, each being secured at its free end to the adjusting portion 44. Each length of suture 60 attaches to a first tang 84 of the adjusting portion 44, passes through the aligned holes 46 and 42 (in a first tang of the abutment portion 40) and through the sewing ring 24 to a first commissure post 26. From there, the suture 60 continues axially to the tip 62 of the post 26, and extends across the outflow side of the valve 22 to the tip of a second commissure post 26. The suture then passes proximally along the second commissure post 26, again through sewing ring 24, and through aligned holes 42 and 46 in second tangs 72, 84, respectively, of the abutment portion 40 and adjusting portion 44. It should be noted that each of the commissure posts 26 desirably has a fabric covering, and the sutures 60 pass at least once through the fabric covering at the tip 62 of each post.

At one of its free ends, the suture 60 passes between the suture grooves 90 within one of the cutting grooves 86. Each length of suture 60 is secured at both ends to different through holes 46 in the adjusting portion 44. Additionally, each two adjacent lengths of suture 60 are secured to the same through hole 46. That is, as seen in FIG. 1, two lengths of suture, 60a and 60b, are seen extending along the closest commissure post 26 to the adjusting portion 44. The first length 60a passes through the left through hole 46b, over the cutting guide 86, and is secured to the right through hole 46b. The second length 60b is secured to the right through hole 46b and passes distally through sewing ring 24 to the commissure post 26. The second length 60b does not cross the cutting guide 86, but instead continues to the next commissure post 26 before extending proximally to the holder 20 and over its associated cutting guide 86. In this manner, the lengths of sutures 60 can be completely disengaged from the valve 22 by simply making three scalpel cuts in each of the three cutting guides 86.

The holder 20 of the present invention works in conjunction with a delivery handle 110, as seen in FIGS. 2 and 4. As seen in FIG. 4, the handle 110 includes a shaft 112 terminating in a distal externally threaded rod 114. The adjusting member 50 is tubular and includes internal threads 116 that are sized and configured to receive the threaded rod 114. In addition, as mentioned above, the adjusting member 50 is externally threaded so as to mate with internal threads 54 on the boss 48 of the adjusting portion 44. By coupling the adjusting member 50 to the boss 48, and then the handle 110 to the adjusting member, the handle 110 connects to the holder 20.

With reference to FIGS. 6A and 6B, use of the holder 20 to radially constrict the commissure posts 26 is shown.

Specifically, FIG. 6A illustrates the holder 20 assembled to the heart valve 22 using the aforementioned lengths of suture 60. In its relaxed configuration, the adjusting portion 44 lies flush against the abutment portion 42. In this state, the adjusting member 50 is threaded part way into the boss 48 such that a distal end contacts the cavity 78 in the abutment portion 40, but can be further advanced a distance A, as indicated. The handle 110 is shown also part way engaged with the adjusting member 50, with the threaded rod 114 still partly showing.

Now with reference to FIG. 6B, the handle 110 has been completely screwed into the adjusting member 50, at which point further rotation of handle 110 causes relative rotation between the adjusting member 50 and the adjusting portion 44. In other words, actuation of the handle 110 causes relative axial movement between the adjusting member 50 and adjusting portion 44. This axial movement is caused by advancement of the adjusting member 50 within the boss 48, which causes the distal end of the adjusting member to push against the abutment member 42. Because the adjusting member 50 is thus prevented from relative movement with respect to the abutment member 42, further advancement of the adjusting member causes the adjusting portion 44 to displace away from the abutment portion 42, as indicated by the arrows 120. The adjusting portion 44 rides upward along the adjusting member 50 until it contacts a proximal shoulder 122, with the resulting spacing B between the adjusting portion 44 and abutment portion 42. Because of the attachment of the lengths of suture 60 to the adjusting portion 44, relative movement of the adjusting portion with respect to the abutment portion 42 pulls each length of suture out of the valve 22. This, in turn, causes inward radial contraction of the commissure posts 26, as indicated by the arrows 124.

In a preferred embodiment, the frictional resistance to rotation between the adjusting member 50 and the adjusting portion 44 is greater than the frictional resistance to rotation between the handle 110 and the adjusting member 50. Consequently, once the commissure posts 26 have been radially constricted, as indicated in FIG. 6B, the handle 110 can be removed (unscrewed) from within the adjusting member 50 without causing relative rotation between the adjusting member and the adjusting portion 44. Therefore, the holder 20 maintains the radially constricted configuration of the commissure posts 26. This inequality in frictional rotation can be obtained in a number of ways. For example, the threaded rod 114 and associated internal threads 116 of the adjusting member 50 have a smaller diameter than the external threads 52 and associated internal threads 54 of the boss 48. Simply by virtue of this size relationship, and corresponding lower surface area in contact, less resistance to rotation of the threaded connection between handle 110 and adjusting member 50 is obtained, all else being equal.

To insure the handle 110 can be removed without reversing the adjusting member 50 with respect to the adjusting portion 44, however, the materials are chosen to enhance the inequality in frictional resistance, as mentioned above. That is, the materials of the adjusting member 50 and adjusting portion 44 are chosen so as to have a greater frictional resistance to relative sliding movement than between the materials of the handle 110 and adjusting member 50. In one embodiment, the adjusting member 50 and adjusting portion 44 are made of the same or different polymers, while handle 110 is metal. Resistance to relative sliding movement between metal and polymer is generally less than that between two polymers. In a preferred embodiment, both the adjusting member 50 and adjusting portion 44 are made of DELRIN, while handle 110 is made a stainless-steel.

FIGS. 7A–7C illustrate several steps in the use of the valve holder 20 the present mentioned. FIG. 7A illustrates a portion of the heart H in cross-section, and specifically the left ventricle LV into which the mitral annulus MA opens. A plurality of sutures 130 is shown pre-installed within the mitral annulus MA. In a typical procedure, the sutures 130 are brought outside the body and passed through the sewing ring 24 of the prosthetic valve 22. The handle 110 attaches to the holder 20 of the present invention which in turn is coupled to the valve 22 and operably engaged therewith to radially constrict the commissure posts 26. During delivery of the valve 22, this radial constriction of the commissure posts 26 helps prevent entangled of the posts with the array of pre-installed sutures 130. Indeed, the access passageway to the mitral annulus MA can be somewhat narrow and nonlinear, making the possibility of suture entanglement problematic. However, radial constriction of the commissure posts 26, in conjunction with the barrier provided by the triangular suspension of sutures 60 between the commissure posts, greatly reduces the chance of entanglement. Moreover, the sutures 130 are entirely prevented by the triangular suspension of sutures 60 from contacting the valve leaflets 28. Not only does the radial constriction of the commissure posts 26 reduce the chance of suture entanglement, but it also reduces the chance of contacting one of the posts with the surrounding anatomy.

After all the sutures 130 have been pre-installed in the mitral annulus MA and threaded through the sewing ring 24, the valve 22 is lowered along the plurality of sutures 130 so that the sewing ring 24 contacts and lies flush against the mitral annulus MA, as seen in FIG. 7B. At this stage, the handle 110 is removed from the holder 20 to facilitate tying off of each of the sutures 130 to secure the valve 22 against the mitral annulus MA. Again, removal of the handle 110 is facilitated by the small frictional resistance to rotation between the handle and holder 20, relative to that between the actuating portions of the holder.

Finally, after securing the valve 22 within the mitral annulus MA, each of the lengths of suture 60 is severed at the cutting guides 86 to facilitate removal of the holder 20 from the valve 22. FIG. 7C shows the severed free ends of the points of suture 60 being pulled from within the valve 22. The holder 20 can be removed using forceps, or handle 110 may be reattached to facilitate the removal.

The present invention contemplates a number of different structures that cause constriction of tissue-type valve commissure posts using a handle, while also permitting removal of the handle without releasing the commissure posts. FIGS. 8A and 8B illustrate a second embodiment of a holder 150 that utilizes a ratchet methodology. Without going into great detail concerning elements of the holder 150 that are similar to those described above, the alternative holder relies on one or more toothed or ratchet members 152 extending proximally from the abutment portion 40 to engage complementary opening(s) in the adjusting portion 44. As the adjusting portion 44 is displaced away from the abutment portion 42, ratchet members 152 retain that spacing, as indicated FIG. 8B. In this way, the relative frictional rotation between handle 110, adjusting portion 44, and adjusting member 50 is not important. Indeed, the handle 110 and adjusting member 50 can be formed as one-piece, rather than two as shown.

Now with reference to FIGS. 9A–9F and 10, use of a clip 160 as mentioned above to attach to holders 20 of the present invention during shipping and storage of an attached valve is illustrated. As illustrated, each clip 160 includes a generally planar C-shaped disk portion 162 having a semi-circular handle 164 attached thereto. The clip 160 is desirably molded of a suitable polymer, with the handle 164 being formed by a semi-circular strip pivotable with respect to the disk portion 162, with its ends attached by living hinges 165 to a pair of upstanding bosses 166. In this respect, the handle 164 lies generally parallel to the plane of the disk portion 162 until pulled upward by the user.

Figure 10:
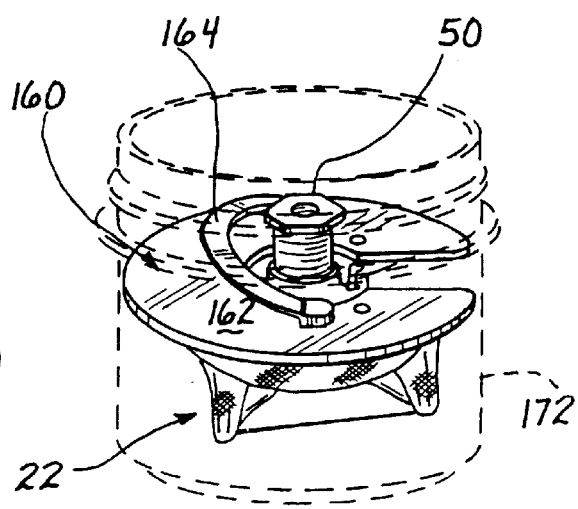
FIG. 10 is a perspective view of the handling clip attached to a holder and valve combination and placed within a storage container shown in phantom.

Three fingers 168 depend downwardly from the disk portion 162 in the direction opposite the direction that the handle 164 may be lifted. Each finger 168 includes an inwardly directed pawl 170 sized to couple with a holder 20 of the present invention. More specifically, the three fingers 168 are circumferentially spaced 120° around a common axis of the holder 20 and clip 160 so as to engage the peripheral notches 100 on the adjusting portion 44 of the holder. As mentioned previously, the peripheral notches 100 for different sized valve holders are radially spaced a consistent distance from the axis. Therefore, the same size clip 160 may be used to couple to a plurality of holders for different sized valves, thus reducing the inventory of clips required. After coupling the clip 160 to the holder 20 (or adjusting member 50), the handle 164 may be used to lower the valve 22 into a storage and shipping container 172, as seen in FIG. 10. The periphery of the disk portion 162 is sized to closely fit within the container 172, and thus prevents the valve from movement in the container during shipping.

The mitral valve holder 20 of the present invention provides an additional advantage over earlier mitral valve holders, such as the holder shown in U.S. Pat. No. 4,865,600 to Carpentier, et al. Specifically, prior holders such as that shown in the Carpentier patent were relatively wide in dimension so as to unnecessarily interfere with attachment of the sutures to the valve and the valve to the annulus.

Figure 11A:
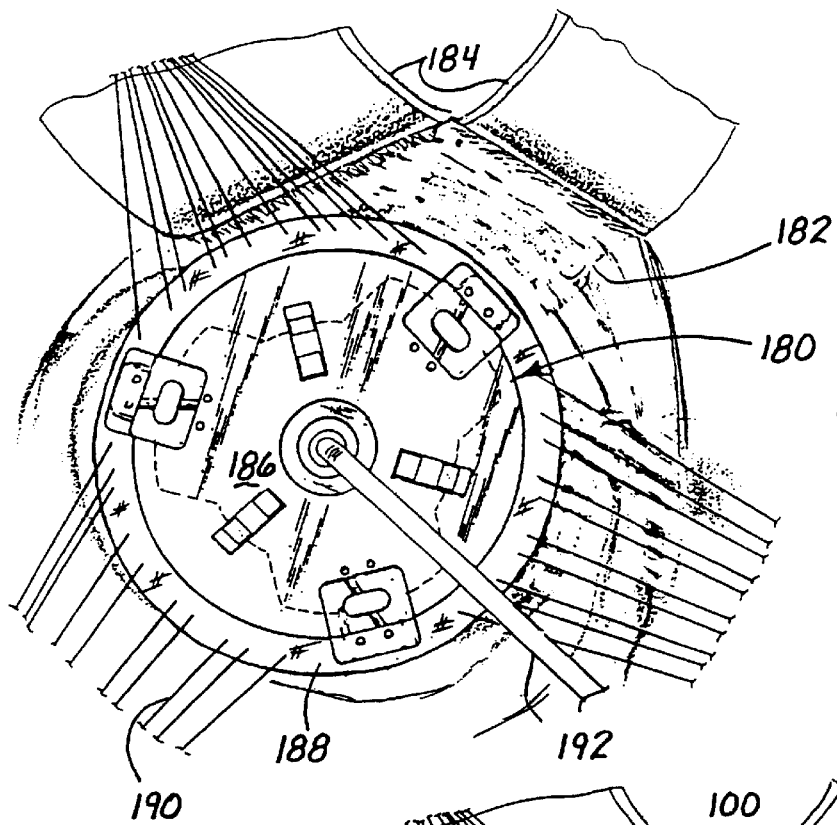
FIG. 11A is a plan view of a heart valve holder of the prior art attached to a heart valve and delivery handle during a step of implantation into a valve annulus.

The holder shown in the Carpentier patent, for example, includes a disk-shaped outer holder plate to which a delivery handle attaches. FIG. 11A illustrates a prior art holder 180 attached to the inflow end of a mitral valve during delivery of the valve into position in an annulus 182. Various means are known for obtaining access to the annulus 22, such as by using a pair of retractors 184 as illustrated to pull surrounding tissue away from surgical field. The outer disk-shaped plate 186 of the holder 180 may be seen occluding all of the mitral valve except for an outer peripheral portion 188 of the sewing ring. A plurality of sutures 190 is shown extending out of the surgical field through the sewing ring 188. These sutures 190 were previously embedded in the annulus 182, and threaded through the sewing ring 188 at a location outside the patient. Though accomplished more conveniently outside the patient, this pre-threading operation must be done after the surgical site has been exposed, and thus time is of the essence. To prevent perivalvular leakage, the array of sutures must be relatively evenly circumferentially spaced and located along a radial line, and this delicate operation may be impeded by the relatively large sized holder body 186, and attendant reduced sewing ring visibility.

After the pre-threading is complete, the surgeon connects a handle 192 to the holder 180 and slides the valve and holder combination down the array of sutures 190 into position in the annulus 182. Because the disk-shaped outer plate 186 is so large, as seen in FIG. 11A, the surgeon cannot see the leaflets from the inflow side of the valve. Problems sometimes arise when the forwardly directed commissures of the valve become entangled in one or more of the sutures in the array. Such entanglement may be visible through the inflow end of the valve, but as mentioned, that view is blocked by the outer plate 186.

Figure 11B:
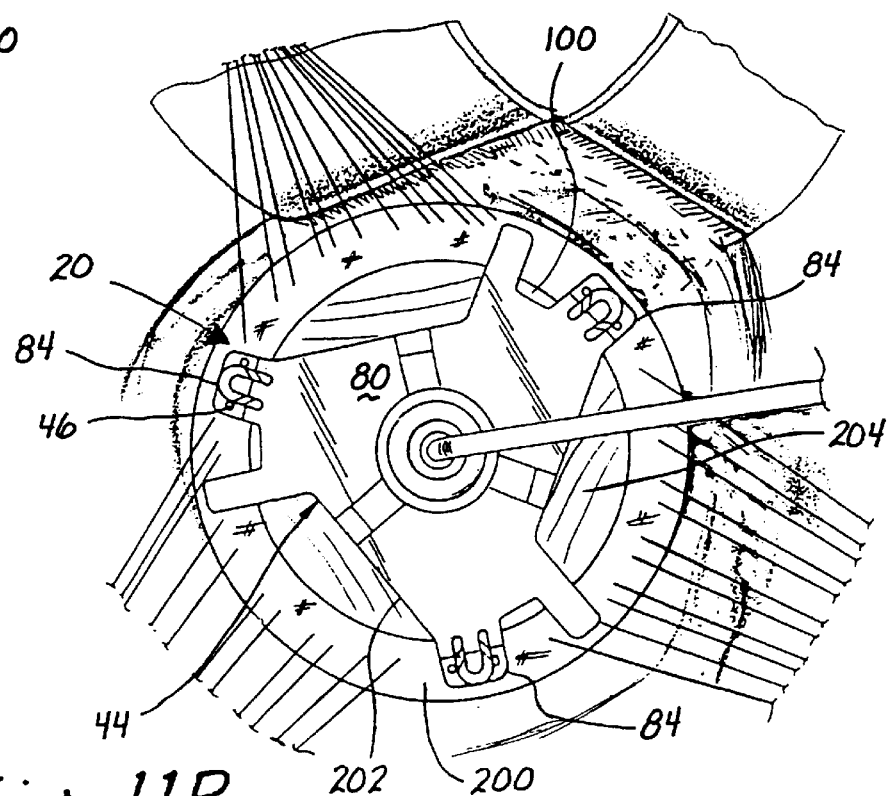
FIG. 11B is a plan view of a heart valve holder of the present invention attached to a heart valve and delivery handle during a step of implantation into a valve annulus.

The present invention provides a holder permitting greater visibility of the valve to help alleviate the aforementioned problems associated with the time-critical processes of pre-threading and then sliding the valve and holder into place. FIG. 11B illustrates the holder 20 of the present invention attached to the inflow end of a prosthetic valve having a peripheral sewing ring 200. The holder 20 is as described above, and like reference numerals for the various elements will be used. Namely, the holder 20 has the approximately triangular-shaped body 80 of the adjusting portion 44 with three outwardly extending tangs 84 at the triangle apices. The tangs 84 feature a pair of through holes 46 through which sutures (not shown for clarity) pass to attach the adjusting portion 44 to the sewing ring 200 of the valve.

The body 80 includes three generally linear sides 202 extending between the tangs 84 (although each side is interrupted by the aforementioned clip-receiving notches 100). The sides 202 separate from and expose the surrounding portions of the sewing ring 200. Indeed, the sides 202 expose the inner volume of the valve, such that leaflets 204 of the valve can be seen from the inflow end thereof. It will therefore be appreciated that the task of pre-threading the array of sutures around the sewing ring 200 is facilitated by the increased visibility of the sewing ring provided by the triangular-shaped holder 20. More specifically, the surgeon can pre-thread the array of sutures around the sewing ring 200 with greater confidence that no sutures are placed too far radially inward or outward, and that they are evenly circumferentially spaced. At a minimum, the time needed to complete this task is reduced. Furthermore, as the valve is introduced to the surgical site along the array of sutures, the surgeon can inspect the leaflets 204 from the inflow side thus enhancing early detection of any suture looping or entanglement that will be visible from the inflow side in the form of a deformed leaflet.

Figure 12A:
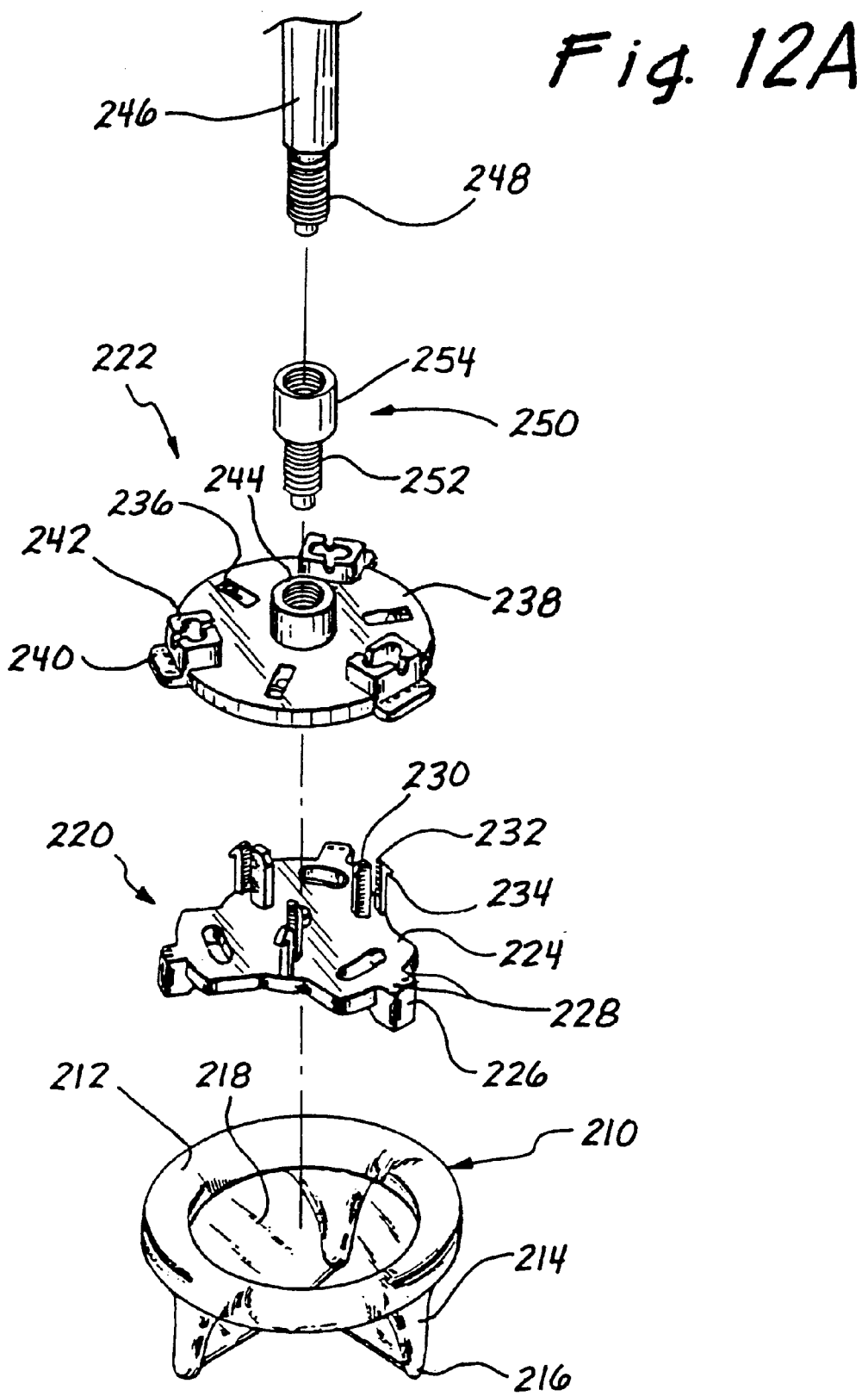
FIG. 12A is an exploded perspective view of a valve, holder, handle and adapter combination of the present invention.

The present invention may provide an improved valve holder as described above, or adapters as described below may be used to retrofit valve holders of the prior art. In particular, FIGS. 12A–12C and 13A–13C illustrate several embodiments of an adapter system of the present invention for use with a prior art valve holder such as that shown in U.S. Pat. No. 4,865,600 to Carpentier, et al. FIG. 12A shows a tissue-type mitral heart valve 210 having a sewing ring 212, a plurality of upstanding commissures 214 with distal tips 216, and a plurality of tissue-type leaflets 218 forming the occluding surfaces of the valve. A conventional holder such as shown in Carpentier, et al. includes a lower plate 220 configured to abut and attach to the sewing ring 212, and an upper plate 220 that works in conjunction with the lower plate 220 to pull the commissure tips 216 of the valve 210 inward. The lower plate 220 has a generally triangular body 224 having three outwardly projecting tangs 226 each with a pair of through holes 228.

Figure 12C:
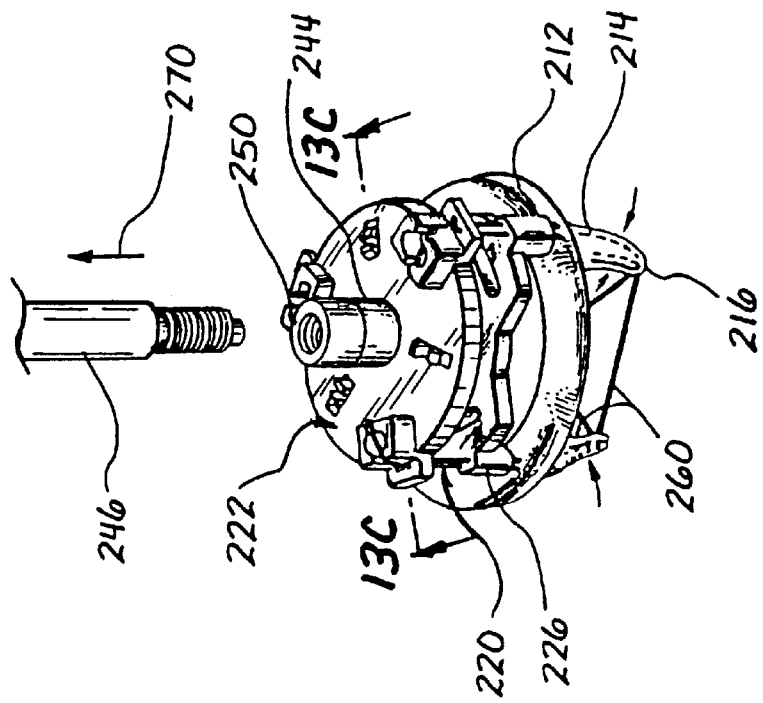
FIGS. 12B–12C are perspective assembled views of the combination of FIG. 12A showing two steps of operation thereof to constrict commissures of the heart valve.
Figure 12B:
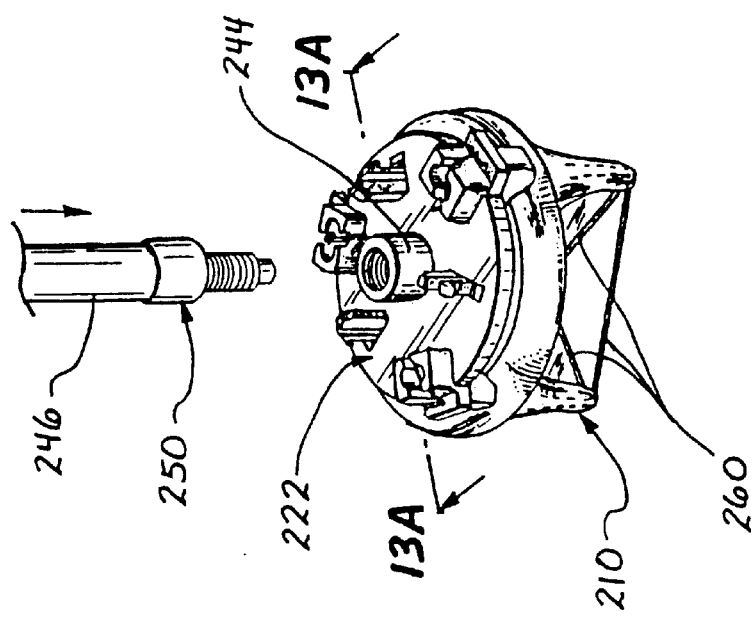

As seen in FIGS. 12B and 12C, three guide posts 230 on the lower plate 220 and three locking posts 232 having outwardly directed pawls 234 pass through and mate with apertures 236 evenly circumferentially spaced around a disk-shaped body 238 of the upper plate 222. The upper plate 222 further includes three outwardly directed flanges 240 having through holes aligned with the through holes 228 in the lower plate 220, and three cutting guides 242 projecting upward from the disk-shaped body 238. In addition, a central internally threaded boss 244 is adapted to receive a delivery handle of the prior art, such as shown at 246 having a male threaded end 248.

The present invention provides an adapter 250 to be interposed between the delivery handle 246 and internally threaded boss 244, having a distal male threaded portion 252 and a proximal female threaded portion 254. The distal male threaded portion 252 is configured to mate with the internally threaded boss 244, while the proximal female threaded portion 254 receives the threaded end 248 of the handle 246.

Use of the adapter 250 is seen best in FIGS. 13A–13C, and generally parallels the function of the adjusting member 50 previously described. As has been described previously, and in the earlier patent to Carpentier, et al., the lower plate 220 and upper plate 222 work in conjunction with the threaded delivery handle to pull the commissure tips 216 inward. FIG. 12C illustrates the two plates 220, 222 separated such that a plurality of sutures connected to the upper plate 222 and passing into the valve and between the commissures (seen at 260) are placed in tension causing the commissure tips 216 to be pulled inward in the direction of the arrows 262. FIGS. 13A–13C illustrate the holder in cross-section and isolated from the valve to better illustrate this plate separation. In contrast to the present invention, in the prior art the delivery handle 246 had to remain threadingly engaged with the upper plate 222 to maintain the plate separation.

In contrast, the adapter 250 of the present invention permits the delivery handle 246 to be removed while maintaining plate separation. FIG. 13A shows the adapter 250 threadingly attached to the delivery handle 246. The combination handle 246 and adapter 250 is then coupled to the upstanding boss 244 on the upper plate 222 and advanced so that a distal end 264 on the adapter contacts a central pin 266 on the lower plate 220. Further advancement of the handle 246 and adapter 250 combination causes separation between the lower and upper plates 220, 222. The separation may be limited by contact between the enlarged proximal portion 254 with the upstanding boss 244, or by engagement of each of the three pawls 234 with corresponding features on the upper plate 222, both shown in FIG. 13B. Subsequently, the delivery handle 246 may be reversed from engagement with the adapter 250 and removed from the surgical site, as seen in FIGS. 12C and 13C. The adapter 250 remains in the position shown in FIG. 13C, maintaining the separation between the lower and upper plates 220, 222, but not interfering with the implantation operation.

There are number of ways to ensure that the handle 246 may be retracted from engagement with the adapter 250 while leaving the adapter in place. For example, and as mentioned above in conjunction with the earlier embodiment, the coefficient of friction between the materials of the engaging threads can be such that the handle 246 can be easily removed. For example, the upper plate 222 is typically molded from a polymer such as Delrin, and the adapter 250 can be formed of a similar material to produce a relatively high coefficient of friction between the respective threads. At the same time, the handle 246 may be made of stainless-steel, for example, which produces a lower coefficient friction between the male threads 248 and the female threads of the proximal adapter portion 254. If the adapter 250 is made a suitable polymer, such as the material of the holder, it may be coupled to the holder prior to packaging, shipping and storage. Many tissue-type heart valves are stored in a preservative solution, such as glutaraldehyde, and material of the holder and adapter 250 must be able to withstand long periods of immersion in such solutions.

Alternatively, the adapter 250 may also be made of stainless-steel, with the relative coefficients of friction being favorable for reversal and removal of the handle 246. In this configuration, the adapter 250 may be sold as a separate article to be coupled with existing delivery handles to retrofit prior art systems. In this manner, both the handle 246 and adapter 250 are able to withstand the high temperatures of steam sterilization, and may be reused.

Another way to ensure that the adapter 250 remains coupled to the upper plate 222 while the handle 246 can be removed is to provide slightly dissimilar thread patterns on the adapter and female threads of the upper plate boss 244. As the handle 246 and adapter 250 are threadingly engaged to the boss 244, the dissimilar threads tend to bind and lock the adapter to the upper plate 222. Consequently, the handle 246 can be easily reversed and de-coupled from the adapter 250.

A still further method of preventing the coupling of the adapter 250 and upper plate 222, while permitting removal of the handle 246, is to provide a groove, raise rib, or similar expedient on the adapter that engages with a mating feature on the upper plate. For example, although not shown, the lower surface of the proximal portion 254 may include a raised radially-directed rib that mates with a groove or similar rib on the upper surface of the boss 244. After the two parts 250, 222 are threadingly engaged, as seen in FIG. 13B, the raised ribs interfere and prevent disengagement, at least to the extent of withstanding the torque applied upon removal of the handle 246 from engagement with the adapter 250.

Figure 14A:
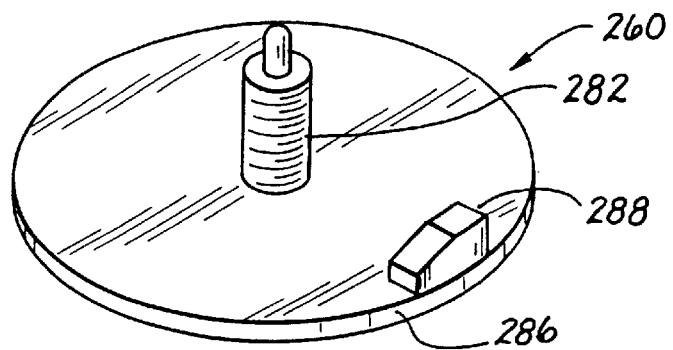
FIGS. 14A–14C are several views of an alternative adapter for use with a valve holder of the present invention.
Figure 14B:
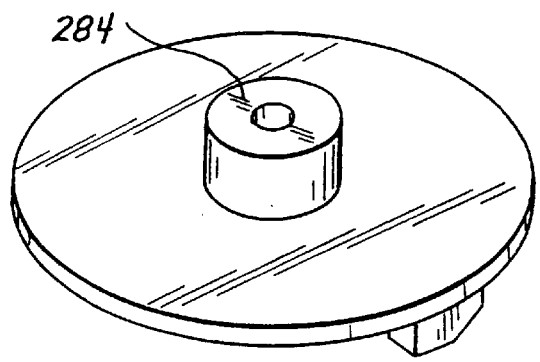
Figure 14C:
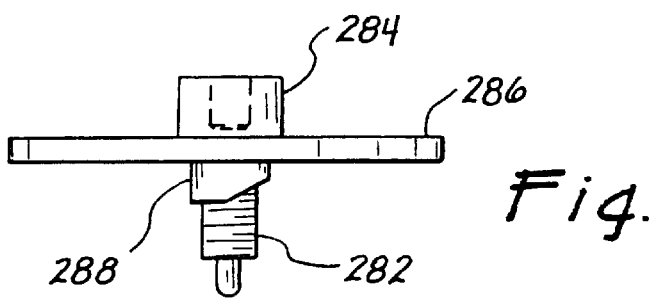

A still further configuration in accordance with the present invention is illustrated FIGS. 14A–14C and 15. In this embodiment, an adapter 280 is provided that includes a distal male threaded portion 282, a proximal female threaded portion 284 and a generally disk-shaped flange 286 interposed therebetween. The flange 286 includes at least one distally-directed tooth or pawl 288 close to a peripheral edge. The adapter 280 is shown in FIG. 14C in an orientation in which it may be coupled with a holder located below, and a handle located above. In particular, the handle will couple to the female threaded portion 284, while the male threaded portion 282 couples with a boss on the holder and causes the aforementioned inward movement of the associated valve commissures.

Figure 15:
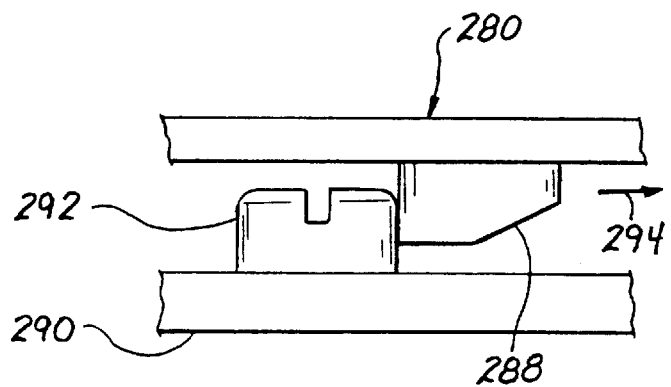
FIG. 15 is a partial elevational view of the interaction between a pawl on the adapter of FIG. 14 and a raised feature on a valve holder to ensure positive engagement therebetween.

FIG. 15 is a partial cutaway that shows engagement of the pawl 288 with an upstanding feature on the valve holder 290, such as a cutting guide 292. That is, rotation of the adapter 280 in the direction of arrow 294 causes the pawl 288 to cam up and over the cutting guide 292. Because of the shape of the pawl 288, the adapter 280 cannot be rotated in the opposite direction. Thus, the adapter 280 is maintained in its threading engagement with the holder, which maintains the aforementioned inward bias of the valve commissures, and permits removal of the handle. The positive engagement of the pawl 288 with the cutting guide 292 ensures that the adapter 280 cannot be removed from the holder once coupled thereto. The illustrated adapter 280 is representative of one type of adapter that can be used to retrofit existing valve holders. Specifically, the adapter 280 can be sold in combination with the valve holder, and be stored with the valve, or can be sold as a separate item to be coupled with handle at the time of surgery.

FIGS. 16A–16F illustrate portions of an alternative holder of the present invention having an alternative structure for maintaining valve commissure constriction. A segment of a valve abutment portion 300 is shown interacting with a segment of an adjusting portion 302. The abutment portion 300 and adjusting portion 302 may in other respects be identical to those illustrated in FIGS. 4 and 5A–5B. Indeed, the abutment portion 300 includes at least one upstanding leg 304 having a hook 306, as described previously. In addition to the leg 304, an upstanding gap retainer 308 is provided, preferably adjacent thereto. The gap retainer 308 includes a stop member 310 having a lower angled surface 312. In preferred embodiment, there are two or more, preferably three, pairs of legs 304 and gap retainers 308. Furthermore, although the leg 304 and gap retainer 308 are illustrated as separate elements, they may be incorporated into a single upstanding element or leg.

FIGS. 16A–16C illustrate a process of assembling the holder by insertion of the leg 304 and gap retainer 308 through an aperture 314 provided in the adjusting portion 302. As seen, the leg 304 and gap retainer 308 are cantilevered and spaced apart so that they may be biased toward one another and fit through the aperture 314. Both the hook 306 and stop member 310 are axially aligned so as to normally interfere with respective sides of the aperture 314, and the leg 304 and gap retainer 308 must be bent to permit passage through the aperture 314.

FIGS. 16D–16F illustrate operation of the holder. FIGS. 16D shows the relative positioning of the valve abutment portion 300 and adjusting portion 302 during storage and shipping of the holder and attached valve. Prior to delivery of the valve along a surgical pathway, the valve abutment portion 300 and adjusting portion 302 are separated so as to constrict the valve commissures, as was described previously. This separation is desirably accomplished using a handle with or without an adapter. As the adjusting portion 302 moves relatively away from the abutment portion 300, depicted in FIG. 16E, the aperture 314 contacts the lower angled surface 312 of the stop member 310 and cams the cantilevered gap retainer 308 inward. Subsequently, the gap retainer, 308 springs upright to its relaxed position, as seen in FIG. 16F, such that the stop member 310 again interferes with and contacts the face of the adjusting portion 302 and prevents it from moving back toward the abutment portion 300. In this manner, a simple and reliable mechanism for maintaining separation of the holder elements provides a positive stop and insurance against inadvertent commissure expansion.

It will be appreciated that the invention has been described hereabove with reference to certain examples or preferred embodiments as shown in the drawings. Various additions, deletions, changes and alterations may be made to the above-described embodiments and examples without departing from the intended spirit and scope of this invention. Accordingly, it is intended that all such additions, deletions, changes and alterations be included within the scope of the following claims.

What is claimed is:

1. A method for profitting a holder for a tissue-type prosthetic mitral heart valve attachable to a surgical delivery handle, the heart valve having an inflow end and an outflow end and a flow axis therebetween, the valve including an annular suture ring at the inflow end and radially flexible commissure posts circumferentially-spaced around the outflow end that support occluding tissue surfaces of the valve, the holder having a commissure post constriction mechanism releasably attached to the suture ring at the inflow end of the valve, the constriction mechanism adapted to constrict the valve commissure posts radially inward from a relaxed position to a constricted position when actuated by the delivery handle, the method including:

providing a retaining mechanism that retains the commissure post constriction mechanism in the constricted position after the delivery handle is removed.

2. The method of claim 1 wherein the step of providing includes providing the retaining mechanism during the holder assembly process so that the retaining mechanism is attached to and shipped as a unit with the prosthetic valve.

3. The method of claim 1 wherein the step of providing includes providing the retaining mechanism separately from the holder and valve combination and the method includes coupling the retaining mechanism to the holder at the time of surgical implantation of the valve.

4. The method of claim 1 wherein the retaining mechanism comprises an adapter that is interposed between and threadingly engaged to the holder and the handle.

* * * * *

UNITED STATES PATENT AND TRADEMARK OFFICE
CERTIFICATE OF CORRECTION

PATENT NO.      : 6,702,852 B2
DATED           : March 9, 2004
INVENTOR(S)     : Robert Stobie et al.

It is certified that error appears in the above-identified patent and that said Letters Patent is hereby corrected as shown below:

<u>Column 16,</u>
Line 11, after "A method for" please delete "profitting" and insert -- retrofitting --.

Signed and Sealed this

Twenty-second Day of June, 2004

JON W. DUDAS
*Acting Director of the United States Patent and Trademark Office*